US009248186B2

(12) United States Patent
Binder

(10) Patent No.: US 9,248,186 B2
(45) Date of Patent: *Feb. 2, 2016

(54) COMPOSITION AND METHOD FOR TREATING NOSEBLEEDS

(71) Applicant: BINYARCO, LLC, Bentleyville, OH (US)

(72) Inventor: Jeffrey E. Binder, Bentleyville, OH (US)

(73) Assignee: BINYARCO, LLC, Bentleyville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,943

(22) Filed: Oct. 30, 2012

(65) Prior Publication Data

US 2013/0052251 A1 Feb. 28, 2013

Related U.S. Application Data

(63) Continuation of application No. 11/122,894, filed on May 5, 2005, now Pat. No. 8,304,402.

(51) Int. Cl.
*A61K 31/715* (2006.01)
*A61K 45/06* (2006.01)
*A61K 31/137* (2006.01)
*A61K 31/29* (2006.01)
*A61K 31/4164* (2006.01)

(52) U.S. Cl.
CPC .............. *A61K 45/06* (2013.01); *A61K 31/137* (2013.01); *A61K 31/29* (2013.01); *A61K 31/4164* (2013.01)

(58) Field of Classification Search
USPC .......................................................... 514/54
See application file for complete search history.

(56) References Cited

U.S. PATENT DOCUMENTS

| 4,801,454 | A | 1/1989 | Coveney |
| 4,820,266 | A | 4/1989 | Berry |
| 4,940,695 | A | 7/1990 | Coveney et al. |
| 4,970,240 | A | 11/1990 | Kielley |
| 5,013,560 | A | 5/1991 | Stentz et al. |
| 5,801,199 | A * | 9/1998 | Greve et al. ............ 514/563 |
| 5,899,918 | A | 5/1999 | Knott et al. |
| 6,162,241 | A | 12/2000 | Conry et al. |
| 6,232,341 | B1 | 5/2001 | Chen et al. |
| 2002/0197302 | A1 * | 12/2002 | Cochrum et al. .......... 424/445 |
| 2004/0267180 | A1 | 12/2004 | Beaudry |

FOREIGN PATENT DOCUMENTS

| GB | 335405 A | 9/1930 |
| JP | H04505267 A | 9/1992 |
| JP | 2001513368 A | 9/2001 |
| JP | 2003531850 A | 10/2003 |
| JP | 2006-514109 A | 4/2006 |
| WO | 9014110 A1 | 11/1990 |
| WO | 9907417 A1 | 2/1999 |
| WO | 0182896 A1 | 11/2001 |
| WO | 2004/056305 A2 | 7/2004 |

OTHER PUBLICATIONS

P.J. Wormald, et al., "Bismuth Subgallate: A Safe Means to a Faster Adeno-Tonsillectomy"; The Journal of Laryngology and Otology, Sep. 1994, vol. 108, pp. 761-762.
Vincent Callanan, et al., "The Influence of Bismuth Subgallate and Adrenaline Paste Upon Operating Time and Operative Blood Loss in Tonsillectomy", The Journal of Laryngology and Otology, Mar. 1995, vol. 109, pp. 206-208.
Stephen F. Conley, et al., "Avoidance of Primary Post-Tonsillectomy Hemorrhage in a Teaching Program", Arch Otolaryngol Head Neck Surg.; Mar. 1999, vol. 125, pp. 330-333.
Anthony J. Maniglia, et al., "Adenotonsillectomy a Safe Outpatient Procedure", Arch Otolaryngol Head Neck Surg.; Jan. 1989; vol. 115, pp. 92-94.
Randy C. Hatton, "Drug Information Rounds—Bismuth Subgallate-Epinepherine Paste in Adenotonsillectomies", The Annals of Pharmacotherapy, Apr. 2000; vol. 34, pp. 522-525.
J.E. Fenton, et al., "Bismuth Subgallate—Its Role in Tonsillectomy"; J. Otolaryngol Otol, Mar. 1995, vol. 109, pp. 203-205.
Sharp, J.F., et al., "Combined Study to Assess the Role of Calcium Alginate Swabs and Ligation of the Inferior Tonsillar Pole in the Control of Intra-Operative Blood Loss During Tonsillectomy", Journal of Laryngology and Otology, Mar. 1991, vol. 105, pp. 191-194.
Sorensen, W.T., et al., "Does Bismuth Subgallate Have Haemostatic Effects in Tonsillectomy?", Clinical Otolaryngology, 1999, vol. 24, pp. 72-74.
Tramontina, V.A., et al., "Effect of Bismuth Subgallate (Local Hemostatic Agent) on Wound Healing in Rats, Histological and Historical Findings"; Braz. Dent. J., 2002, vol. 13, pp. 11-16.
Milford, C.A., et al., "The Influence of Calcium Alginate Haemostatic Swabs Upon Operative Blood Loss in Adenotonsillectomy", Clinical Otolaryngology, 1990, vol. 15, pp. 303-306.
Mora LTA, et al., "Efficacy and Safety of Bismuth Subgallate and Salicilate Applied as Hemostatic Agent After Third Molar Extraction", Rev. Adm, 2003, vol. 60(3), pp. 90-94 (Abstract).
Thorisdottir, H., et al., "Activation of Hageman Factor (Factor XII) by Bismuth Subgallate, A Hemostatic Agent", Journal of Laboratory and Clinical Medicine, Oct. 1988, vol. 112, pp. 481-486.
Murray, A., et al., "Respiratory Difficulty Following Bismuth Subgallate Aspiration", Arch Otolaryngol Head Neck Surgery, Jan. 2000, vol. 126, pp. 79-81.
MacDonald, M., et al., "Electrocautery-Induced Ignition of Tonsillar Packing", Journal of Otolaryngology, 1994, vol. 23, No. 6, pp. 426-429.
Code of Federal Regulations, 21 CFR 73.1162, "Bismuth Oxychloride", Apr. 1, 2002, Title 21, vol. 1, pp. 1-2.

(Continued)

*Primary Examiner* — Adam C Milligan
(74) *Attorney, Agent, or Firm* — Pearne & Gordon LLP

(57) ABSTRACT

A composition and method for treating nosebleed, that is, epistaxis. The composition comprises bismuth subgallate and a vasoconstriction agent, preferably oxymetazoline. The composition is preferably a paste administered intranasally.

13 Claims, No Drawings

(56) References Cited

OTHER PUBLICATIONS

Cozzi, L., et al., "Pulmonary Sequelae of Intraparenchymal Bismuth Subgallate", Laryngoscope 102, Jun. 1992, pp. 597-599.

Tannous, W., et al., "Pitfall to Avoid Pharyngeal Opacities Caused by Bismuth Subgallate", J. Can. Assoc. Radiol. 1989, vol. 40, pp. 312.

Committee for Veterinary Medicinal Products, "Bismuth Subnitrate, Bismuth Subcarbonate, Bismuth Subgallate, Bismuth Subsalicylate", European Agency for the Evaluation of Medicinal Products, Apr. 1997, pp. 1-2.

Harris, A., et al., "Letters to the Editors", Aliment. Pharmacol. Ther., 1996, vol. 10, pp. 1035-1036.

NADA 042-841, "General Information", Food and Drug Administration EFOI General Information, Feb. 21, 1991, pp. 1-4.

Corboz, et al., "Pharmacological Characterization of α2-Adrenoceptor-Mediated Responses in Pig Nasal Mucosa", Autonomic and Autacoid Pharmacology, 2003, vol. 23, No. 4, pp. 208-219.

Murray, et al., "Respiration Difficulty Following Bismuth Subgallate Aspiration", Archives of Otalaryngology—Head and Neck Surgery, 2000, vol. 126(1), Abstract.

Cerner Multum, Consumer Drug Information, Oxymetazoline Nasal Medical Facts From drugs.com, 2004, pp. 1-4.

Krempl, G., "Use of Ozymetazoline in the Management of Epistaxis", Ann. Otol. Rhinol. Laryngol., 1995, vol. 104, pp. 704-706.

Benavente, J., "Innovative Tools to Be Used in Epistaxis", 2002, www.sochiorl.cl/indices/pdfs/61-3/13.pdf?PHPSESSID, pp. 1-3.

Crause, J., "Complication of Epistaxis", The British Medical Journal, 1955, 1(4915), p. 726.

Benavente, J., "New Tools for Use in Epistaxis", 2002, www.sochiorl.cl/indices/pdf/61/3/13.pdf, Translation, pp. 1-3.

Epistaxis Therapy, "Therapeutic Intranasal Drug Delivery", www.intranasal.net/epistaxis/default.htm, pp. 1-8, Apr. 21, 2011.

Sharp, J., et al., "The Role of Calcium Alginate (CA) Swabs in Tonsillectomy", Clinical Otolaryngology and Allied Sciences, 1991, vol. 16, p. 319.

Kotecha, B., et al., "Management of Epistaxis: A National Survey", Ann. R. Coll. Surg. Engl. 1996, vol. 78, No. 5, pp. 444-446.

* cited by examiner

COMPOSITION AND METHOD FOR TREATING NOSEBLEEDS

FIELD OF THE INVENTION

The invention relates generally to medical care and more specifically to compositions and methods for treating nosebleeds, that is, treating epistaxis.

BACKGROUND OF THE INVENTION

Nosebleed, scientifically called epistaxis, is a worldwide problem that often requires medical assistance for control. Inhaling air often has an excessive drying effect on the delicate moist nasal mucous membranes that line a person's nose, leaving the highly vascular nasal membranes susceptible to cracking, erosion and local mechanical trauma with subsequent nosebleeding or epistaxis. Blunt trauma to the nose, sneezing, and other things can cause nosebleeds. While some bleeding is arterial and profuse, the overwhelming majority of human nosebleeds are light and located in the forward area of the nose that is accessible through the nostrils and frequently recurrent.

The reported incidence of epistaxis ranges from 7% to 60% of the population, with only 6% seeking medical attention. The frequency of nosebleeding or epistaxis is expected to increase due to people living in dry environments, nasal allergies, local nasal irritants such as pollutants, and the increasing use of aspirin and other drugs that reduce or affect blood clotting.

Despite the worldwide and frequent nature of epistaxis, little is currently available for immediately available treatment. Anecdotal treatments include pinching the nose, ice packs to the face or neck and holding the head in a-downward dependent position. Several mechanical devices for non-medical personnel have been described and largely rely on applying pressure to the inside of the nose through various devices such as intranasal balloon insufflation, clamping instruments or soft intranasal sponges that are placed alongside the site of bleeding to apply mechanical pressure. Physicians often cauterize sites of nasal bleeding using electric and chemical agents. Unpredictable bleeding sometimes develops after the cautery attempt and frequently nasal packing is placed to help control future bleeding. Calcium alginate coated on an intranasal sponge has been suggested as a treatment for epistaxis.

SUMMARY OF THE INVENTION

A method for treating epistaxis, the method comprising a step of administering to a patient suffering from epistaxis an effective amount of a composition comprising bismuth subgallate and a vasoconstriction agent. A composition for treating epistaxis is provided. The composition comprises bismuth subgallate and a vasoconstriction agent. The composition is effective for treating epistaxis when applied topically to a patient suffering from epistaxis. Bismuth subgallate is present in the composition in a weight percent effective to assist in slowing or stopping epistaxis. The vasoconstriction agent is present in the composition in a weight percent effective to assist in slowing or stopping epistaxis. The weight percent of bismuth subgallate and the weight percent of the vasoconstriction agent are effective, in combination, to slow or stop epistaxis when the composition is administered to a patient suffering from epistaxis.

DETAILED DESCRIPTION OF THE PREFERRED EMBODIMENTS OF THE INVENTION

As used herein, when a range such as 5-25 or 5 to 25 is given, this means preferably at least 5 and, separately and independently, preferably not more than 25.

A vasoconstriction agent is an agent which causes a narrowing of the lumen of blood vessels and includes those vasoconstriction agents known in the art, including epinephrine, phenylephrine, oxymetazoline, norepinephrine, phenylpropanolamine, pseudoephedrine, naphazoline, xylometazoline, propylhexedrine, levodesoxyephedrine, ephedrine, adrenochrome, tetrahydrozoline, and mixtures of the foregoing.

The invented pharmaceutical composition for hemostatic effect comprises bismuth subgallate and a vasoconstriction agent. Bismuth subgallate is a saffron-yellow powder which is insoluble in water and which has the formula $C_6H_2(OH)_3COOBi(OH)_2$. It is available from Mallinckrodt Baker, Inc. as Mallinckrodt Prod. No. 0304, which is 90-100% by weight bismuth subgallate. It's CAS No. is 99-26-3. Bismuth subgallate is generally available as a relatively pure powder, for example, 70% to 80% to 90% to 95% to 98% to 99% to 100% pure bismuth subgallate by weight.

The vasoconstriction agent is preferably epinephrine, phenylephrine, oxymetazoline, norepinephrine, phenylpropanolamine, pseudoephedrine, naphazoline, xylometazoline, propylhexedrine, levodesoxyephedrine, ephedrine, adrenochrome, tetrahydrozoline, and mixtures thereof, more preferably those vasoconstriction agents which exhibit vasoconstrictive effect for longer than two hours after intranasal application, more preferably those vasoconstriction agents which exhibit vasoconstrictive effect for as long or longer than phenylephrine exhibits vasoconstictive effect after intranasal application, more preferably oxymetazoline. Vasoconstriction agents are generally available in a dilute aqueous solution (a concentrated solution might act too quickly or too much), preferably at a concentration of 0.00001-10 weight percent, more preferably 0.001-1 weight percent, more preferably 0.01-0.1 weight percent, preferably in aqueous liquid or aqueous solution. A preferred vasoconstriction agent is a 0.05% oxymetazoline aqueous solution.

The invented composition is preferably a paste formed with water, preferably a soft and malleable paste capable of being easily spread into a thin layer, such as 0.01-4 or 0.05-3 or 0.2 to 2 or 0.5 to 1.5 or about 1, mm thick, using a butter knife, finger, or other instrument; the paste is preferably applied intranasally at these preferred thicknesses. A soft paste such as this can be more easily spread onto a pledget or sponge and applied intranasally into the bleeding nostril so that the paste is applied topically to the bleeding nasal mucous membranes. The soft paste is preferably made by mixing bismuth subgallate powder with a vasoconstriction agent in aqueous solution as described above, for example 0.01-5, more preferably 0.1-3, more preferably 0.3-2, more preferably 0.4-1.3, more preferably 0.5-1, more preferably about 0.7, ml of vasoconstriction agent in aqueous solution per 1 gram of bismuth subgallate powder such as Mallincknodt Prod. No. 0304. The composition is preferably 3-99.999999, more preferably 25-95, more preferably 40-80, more preferably 50-70, weight percent bismuth subgallate (i.e., in paste form), and 0.00001-20, more preferably 0.0001-2, more preferably 0.002-0.2, weight percent vasoconstriction agent (water being considered not a vasoconstriction agent). The invented composition preferably consists of or consists essentially of commercially available bismuth subgallate powder mixed with commercially available vasoconstriction agent (preferably in aqueous solution), but alternatively or less preferably other ingredients can be added, such as carriers, fillers, diluents, extenders, thickening agents, etc., as known in the art, such as corn starch, talc, etc. Alternatively calcium alginate can be added, preferably at a rate of 0.1-10 or 0.5-10 or 1-10 parts by weight of calcium alginate per 10 parts by weight of bismuth subgallate. Additional water may be needed to form a suitable paste, but it is preferred that the paste is thinned by adding more vasoconstriction agent in aqueous solution. The paste may be thickened by adding more bismuth subgallate powder, or by letting the paste partially or completely dry, or by adding thickening agents or drying agents.

To administer the composition to a patient suffering epistaxis to stop or slow nasal bleeding, preferably the paste is prepared by mixing bismuth subgallate powder with a dilute vasoconstriction agent liquid, preferably 0.05% oxymetazoline or the other vasoconstriction agents mentioned above, to form a paste. The paste can be disposed or provided or applied or coated or spread onto an applicator device and the applicator device can be applied intranasally so that the paste is mechanically pressed against the bleeding site. Preferred applicator devices include applicators (such as cotton-tipped, sponge-tipped or fibrous-tipped applicators) and other applicator devices such as pledgets, nasal packs, nasal sponges (also called nasal tampons), and other nasal packing materials. The pressure from the applicator device, such as applicator, pledget or sponge, will force a coating of the paste against the bleeding surface. Also, the paste can be applied to a nasal packing material or nasal packing and inserted into the nose, or the paste can be supplied in a container and the patient can apply the paste intranasally by use of an applicator device such as an applicator such as a cotton-tipped applicator. Alternatively the composition can be prepared and applied topically and pressed mechanically intranasally against the bleeding site using other techniques and devices as is known in the intranasal treatment art.

An effective amount of the composition is applied, that is, enough of the composition to slow or stop epistaxis. Bismuth subgallate and vasoconstriction agent are each present in a weight percent effective to assist in slowing or stopping epistaxis. The weight percent of bismuth subgallate and the weight percent of vasoconstriction agent are effective, in combination, to slow or stop epistaxis. If an element in a composition provides more benefit or measurably more benefit as compared to the same composition without the element, the element is present in a weight percent effective to assist in slowing or stopping epistaxis.

EXAMPLES

In all of the examples a paste was applied which was made by mixing about 1 g bismuth subgallate powder with about 0.7 ml of 0.05% oxymetazoline in aqueous solution.

Example 1

A 78 year old male on daily 81 mg of aspirin had a habit of chronic nose picking which caused subsequent nose bleeding. An intranasal pledget was coated with the above-mentioned paste and was placed intranasally and was removed 24 hours later with no recurrent bleeding.

Example 2

A 50 year old white female suffered from recurrent nosebleed of unpredictable onset and frequency. The area of bleeding was identified and cauterized using silver nitrate. A nasal pack was coated with the above-mentioned paste and was placed intranasally and removed 4 hours later. No mucous membrane reaction was found and no further bleeding developed.

Example 3

A 58 year old female with a history of stroke that required anticoagulant therapy fell at home breaking her nose and developing a nosebleed. A conventional nasal pack was placed with incomplete control of bleeding after 18 hours. The original pack was replaced with a pack coated with the above-mentioned paste. The pack was removed approximately 12 hours later with no further bleeding. The results of these Examples was surprising and unexpected.

Although preferred embodiments of the invention have been described, it is contemplated that modifications thereof may be made and some features may be employed without others. All such variations are considered within the scope of this invention as defined by the appended claims.

What is claimed is:

1. A method for treating epistaxis in a human, said method comprising a step of administering to a human patient suffering from epistaxis an effective amount of a composition comprising 0.4-1.3 ml of 0.05% oxymetazoline aqueous solution per 1 gram of bismuth subgallate powder, said composition being effective for treating epistaxis in a human when administered to a human patient suffering from epistaxis, said bismuth subgallate being present in said composition in a weight percent effective to assist in slowing or stopping epistaxis, said oxymetazoline being present in said composition in a weight percent effective to assist in slowing or stopping epistaxis, said weight percent of bismuth subgallate and said weight percent of said oxymetazoline being effective, in combination, to treat epistaxis when said composition is administered to a human patient suffering from epistaxis.

2. The method of claim 1, wherein said composition is a paste.

3. The method of claim 1, wherein said composition further comprises calcium alginate.

4. The method of claim 1, said step of administering including administering topically and intranasally.

5. The method of claim 4, wherein said step of administering includes providing said composition disposed on an applicator device and then applying said applicator device intranasally to said patient.

6. The method of claim 5, wherein said applicator device is selected from the group consisting of applicators, pledgets, nasal tampons, and nasal packs.

7. A composition for treating epistaxis in a human, said composition comprising 0.4-1.3 ml of 0.05% oxymetazoline aqueous solution per 1 gram of bismuth subgallate powder, said composition being effective for treating epistaxis in a human when administered to a human patient suffering from epistaxis, said bismuth subgallate being present in said composition in a weight percent effective to assist in slowing or stopping epistaxis, said oxymetazoline being present in said composition in a weight percent effective to assist in slowing or stopping epistaxis, said weight percent of bismuth subgallate and said weight percent of said oxymetazoline being effective, in combination, to treat epistaxis when said composition is administered to a human patient suffering from epistaxis.

8. The composition of claim 7, wherein said composition is a paste.

9. The composition of claim 7, wherein said composition further comprises calcium alginate.

10. The composition of claim 7, further comprising an applicator device, said composition being disposed on said applicator device.

11. The composition of claim 7, further comprising an applicator device, said composition being disposed on said applicator device, said applicator device being selected from the group consisting of applicators, pledgets, nasal tampons, and nasal packs.

12. The composition according to claim 7, wherein said composition comprises about 0.7 ml of 0.05% oxymetazoline aqueous solution per 1 gram of bismuth subgallate powder.

13. The method according to claim 1, wherein said composition comprises about 0.7 ml of 0.05% oxymetazoline aqueous solution per 1 gram of bismuth subgallate powder.

* * * * *